United States Patent
Slepnev et al.

(10) Patent No.: US 9,856,514 B2
(45) Date of Patent: *Jan. 2, 2018

(54) METHODS OF NUCLEIC ACID FRACTIONATION AND DETECTION

(71) Applicant: Meridian Bioscience, Inc., Cincinnati, OH (US)

(72) Inventors: Vladimir I Slepnev, Cincinnati, OH (US); Ahmer Kodvawala, Cincinnati, OH (US); Brian Loeffler, Cincinnati, OH (US); Anand Hindupur, Cincinnati, OH (US); Reddy Ponaka, Cincinnati, OH (US); Vecheslav A. Elagin, Cincinnati, OH (US)

(73) Assignee: Meridian Bioscience, Inc., Cleveland, OH (US)

( * ) Notice: Subject to any disclaimer, the term of this patent is extended or adjusted under 35 U.S.C. 154(b) by 451 days.

This patent is subject to a terminal disclaimer.

(21) Appl. No.: 14/546,478

(22) Filed: Nov. 18, 2014

(65) Prior Publication Data

US 2015/0079601 A1 Mar. 19, 2015

Related U.S. Application Data

(63) Continuation of application No. PCT/US2013/042671, filed on May 24, 2013.

(60) Provisional application No. 61/651,426, filed on May 24, 2012.

(51) Int. Cl.
C12Q 1/68 (2006.01)

(52) U.S. Cl.
CPC .................. *C12Q 1/6806* (2013.01)

(58) Field of Classification Search
CPC .................................... C12Q 1/6806
USPC ........................................ 435/6.12
See application file for complete search history.

(56) References Cited

U.S. PATENT DOCUMENTS 5,622,822 A 4/1997 Ekeze et al.

FOREIGN PATENT DOCUMENTS

| CN | 102827829 A | 12/2012 |
|---|---|---|
| WO | 2007/140417 A2 | 12/2007 |
| WO | 2011/124705 A1 | 10/2011 |
| WO | 2011/124709 A1 | 10/2011 |

OTHER PUBLICATIONS

European Office Action for EP Application No. 13 79 4485 dated Jul. 8, 2016 (6 pages).
European Supplementary Search Report for EP Application No. 13 79 4485 dated Nov. 12, 2015 (8 pages).
Shiloff et al., "Monoamine Oxidase B Isolated from Bovine Liver Exists as Large Oligomeric Complexes in vitro," Eur. J. Biochem, 1996, 242:41-50.
Truett et al., "Preparation of PCR-Quality Mouse Genomic DNA with Hot Sodium Hydroxide and Tris (HotSHOT)," Bio Techniques, 2000, 29(1) (2 pages).
PCT International Search Report and Written Opinion for PCT Application No. PCT/US2013/042671 dated Aug. 25, 2014 (17 pages).

*Primary Examiner* — Jezia Riley
(74) *Attorney, Agent, or Firm* — Eversheds Sutherland (US) LLP

(57) ABSTRACT

The invention provides methods of detecting a nucleic acid present in a biological sample, comprising combining the biological sample with a lysis buffer to form a lysis mixture comprising nucleic acid released from cells in said biological sample; and subjecting a volume of the lysis mixture to size-exclusion chromatography in a column comprising a volume of size-exclusion medium. In certain embodiments, the lysis buffer separates double-stranded nucleic acid into single-stranded nucleic acid. In certain embodiments, the elution can have a flow rate of separation of less than 10 minutes to produce an eluted solution comprising isolated nucleic acid. The invention provides for a method of accurately and rapidly detecting products of nucleic acid amplification.

33 Claims, 3 Drawing Sheets

METHODS OF NUCLEIC ACID FRACTIONATION AND DETECTION

CROSS REFERENCES TO RELATED APPLICATIONS

This application is a continuation application of PCT Application No. PCT/US2013/042671 filed on May 24, 2013 which claims the benefit of U.S. Provisional Patent Application No. 61/651,426, filed May 24, 2012, which are hereby incorporated by reference in their entirety.

FIELD OF INVENTION

The present invention relates to methods of isolation and purification of nucleic acids from a biological sample or matrix. More particularly, the present invention relates to the isolation and purification of nucleic acids using size-exclusion or gel filtration chromatography.

BACKGROUND OF THE INVENTION

The isolation and identification of nucleic acids are important steps in many biochemical detection and clinical diagnostic tests. The separation of nucleic acids from the complex cellular compositions in which they are found is often a necessary initial step before detection or amplification can be undertaken. The presence of large amounts of cellular debris, such as proteins and carbohydrates, in the compositions often impedes the reactions and techniques used in molecular biology. The presence of exogenous agents frequently used for nucleic acid isolation can also inhibit nucleic acid amplification. Therefore, the current isolation and amplification procedures are undesirably time consuming, complicated, and inefficient. Thus, improved methods for the isolation and detection of nucleic acids, are desirable, for a broad variety of applications in medical diagnostics for microbial infections, detection of genetic variations, forensic science, tissue and blood typing, detection of environmental pathogens, and basic research, to name a few.

A range of methods are known for the isolation and purification of nucleic acids, but generally, these rely on a complex series of extraction and washing steps and are time consuming and laborious to perform. Classical methods for the isolation of nucleic acids from complex starting materials, such as blood, blood products, tissues, or other biological materials, involve lysis of the biological material, followed by isolation strategies such as solid phase extraction or phenol extraction followed with ethanol precipitation.

Paramagnetic bead technology has also been used for nucleic acid isolation. Most magnetic bead-based methods rely on lysing the sample followed by binding nucleic acids with magnetic beads and washing. Isolated nucleic acids obtained from these methods often contain agents, such as ethanol, which inhibit further amplification and detection.

Size-exclusion chromatography (SEC), also called gel-filtration or gel-permeation chromatography (GPC), uses porous particles stacked within a column to separate molecules of different sizes. It is generally used to separate biological molecules, and to determine molecular weights and molecular weight distributions of polymers. Molecules that are smaller than the pore size can enter the particles and therefore have a longer path and longer transit time than larger molecules that cannot enter the particles. Molecules larger than the pore size can not easily enter the pores, and elute together earlier in the chromatogram. Molecules that can enter the pores have an average residence time in the particles that depends on the molecular size and shape. Different molecules therefore have different total transit times through the column.

There is still a need for improved nucleic acid purification and detection methods which are quick, economical and simple to perform, which enable detectable yields to be obtained with minimal losses, whereby the nucleic acids obtained are ready for downstream amplification and analysis.

SUMMARY OF THE INVENTION

In certain embodiments, the invention provides a method of detecting a nucleic acid present in a biological sample, comprising the steps of: a) combining the biological sample with a lysis buffer to form a lysis mixture comprising nucleic acid released from cells in said biological sample; b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than 10 minutes to produce an eluted solution comprising isolated nucleic acid; c) combining the eluted solution with nucleic acid amplification reagents comprising DNA polymerase, oligonucleotides and nucleoside triphosphates for nucleic acid amplification; d) amplifying the nucleic acid in the eluted solution; and e) detecting products of nucleic acid amplification.

The present invention also provides a method of purifying a nucleic acid from a biological sample, comprising the steps of: a) combining the biological sample with a lysis buffer to form a lysis mixture comprising nucleic acid released from cells in said biological sample; and b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than 10 minutes to produce an eluted solution comprising isolated nucleic acid. In certain embodiments, the invention provides the later step of analyzing said isolated nucleic acid using an enzyme-catalyzed reaction.

The present invention further provides a method of purifying a nucleic acid from a biological sample, comprising the steps of: a) combining the biological sample with a denaturing solution that separates strands of double-stranded DNA; b) subjecting a volume of the biological sample mixture to size-exclusion chromatography in a column comprising a volume of size-exclusion medium, wherein said volume of lysis mixture is 0.01 to 0.6 of the volume of the size-exclusion medium, and having a gravity-based flow rate of separation of less than 10 minutes to produce an eluted solution comprising isolated nucleic acid; and c) collecting the eluted solution for further analysis.

In an alternative embodiment, the present invention provides a method of purifying a nucleic acid from a biological sample, comprising the steps of: a) combining the biological sample with a lysis buffer to form a lysis mixture comprising nucleic acid released from cells in said biological sample; b) applying a volume of the lysis mixture to size-exclusion chromatography medium in a column comprising a loading end, an eluting end and a volume of size-exclusion medium, optionally wherein said volume of lysis mixture is 0.35 to 0.8 of the volume of the size-exclusion medium, and allowing the lysis mixture to enter the size exclusion chromatography medium; and c) providing a positive pressure differential to the column to produce an eluted solution containing nucleic acid for subsequent amplification or analysis. In certain embodiments, the pressure differential is created by applying a positive pressure to the loading side of the column. In another embodiment the present invention provides a method of purifying nucleic acids, comprising the steps of: a) applying a volume of a sample containing nucleic acids to size-exclusion chromatography medium in a column comprising a loading end, an eluting end, and a volume of size-exclusion medium, and allowing sample to enter the size-exclusion chromatography medium; and b) providing a negative pressure differential or vacuum to the eluting end of the column and collecting drained fluid containing nucleic acid for further amplification or analysis.

The present invention further provides a method of purifying a nucleic acid from a biological sample, comprising the steps of: a) subjecting a volume of a mixture of biological sample containing nucleic acid and a lysis agent to size-exclusion chromatography in a column comprising a volume of size-exclusion medium, wherein said volume of the mixture is 0.01 to 0.6 of the volume of the size-exclusion medium, and having a gravity-based flow rate of separation of less than 10 minutes to produce an eluted solution comprising isolated nucleic acid; and c) collecting the eluted solution for further analysis.

In certain embodiments, the invention provides further equilibrating said chromatography column with an equilibrating buffer comprising 1-10 mM $Mg^{2+}$ or a non-ionic detergent, or a combination, prior to the subjecting step that essentially will be used for conducting the nucleic acid amplification step. In certain embodiments, the invention provides that the lysis buffer comprises alkali hydroxide at pH>11. In certain embodiments, the invention provides that the lysis buffer comprises urea or chaotropic salts. In certain embodiments, the invention provides that the lysis buffer separates double stranded nucleic acid into single stranded nucleic acid and inhibits nucleic acid interactions with protein.

In certain embodiments, the invention provides that the size-exclusion medium comprises a polymer such as polyacrylamide, polybisacrylamide or polymethacrylamide. In certain embodiments, the invention provides that the size-exclusion medium has a molecular size exclusion limit of about 10 kDa or more. In certain embodiments, the flow rate of separation is gravity-based.

The invention provides that the nucleic acid is either DNA, RNA, or a mixture thereof. The invention further provides that the amplifying step can be selected from the group consisting of RT-PCR, qPCR, digital PCR, LAMP, sequencing, and an enzyme-catalyzed reaction now known—or later developed. In certain embodiments, the invention provides that the biological sample can be selected from any source, including blood, saliva, stool, urine, respiratory sample, or enriched culture broth.

DETAILED DESCRIPTION OF THE INVENTION

Figure 1:
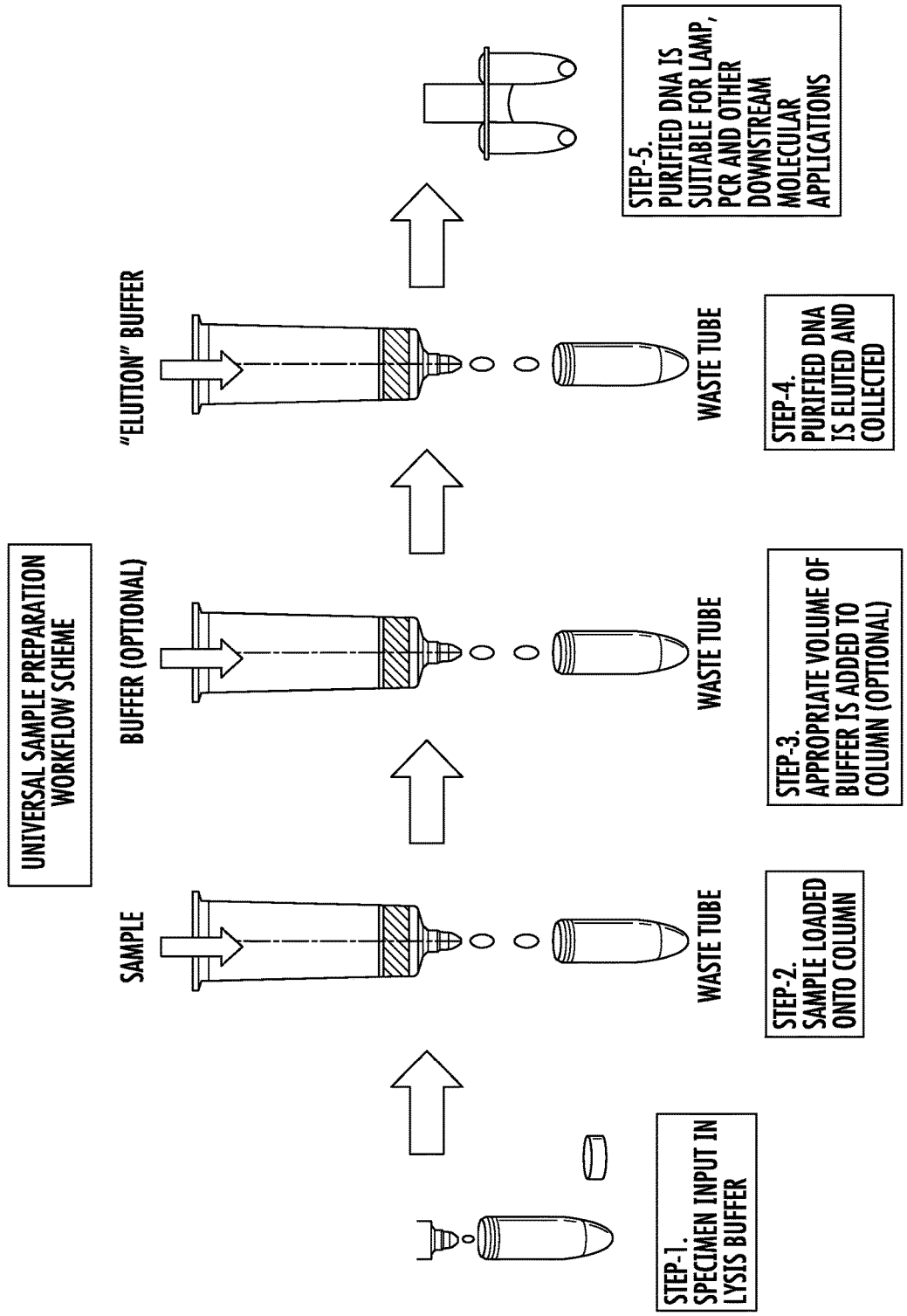
FIG. 1 illustrates a universal sample preparation (USP) workflow scheme.

The present invention provides a universally applicable nucleic acid purification, detection, and amplification method and system using size-exclusion chromatography for separation of nucleic acids from other cellular components. The method and system provides isolated nucleic acids in less time than conventional techniques in a form that is substantially free from other inhibitors of nucleic acid amplification, detection, and/or analysis. The isolated nucleic acid can also be prepared denatured from a double-stranded to a single-stranded form during the purification process, thus, eliminating a heat denaturing step in the subsequent nucleic acid amplification and detection process. These and other advantages and features of the invention will be apparent to one of skill in the art.

In certain embodiments, the invention provides a method of detecting a nucleic acid present in a biological sample, comprising the steps of: a) combining the biological sample with a lysis buffer to form a lysis mixture comprising nucleic acid released from cells in said biological sample; b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than about 10 minutes to produce an eluted solution comprising isolated nucleic acid; c) combining the eluted solution with nucleic acid amplification reagents comprising DNA polymerase, oligonucleotides and nucleoside triphosphates for nucleic acid amplification; d) amplifying the nucleic acid in the eluted solution; and e) detecting products of nucleic acid amplification.

The present invention also provides a method of purifying a nucleic acid from a biological sample, comprising the steps of: a) combining the biological sample with a lysis buffer to form a lysis mixture comprising nucleic acid released from cells in said biological sample; and b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than about 10 minutes to produce an eluted solution comprising isolated nucleic acid. In certain embodiments, the invention provides the later step of optionally amplifying and detecting or analyzing said isolated nucleic acid using an enzyme-catalyzed reaction.

The present invention further provides a method of purifying a nucleic acid from a biological sample, comprising the steps of: a) combining the biological sample with a denaturing solution that separates strands of double-stranded DNA; b) subjecting a volume of the biological sample mixture to size-exclusion chromatography in a column comprising a volume of size-exclusion medium, wherein optionally said volume of lysis mixture is 0.01 to 0.6 of the volume of the size-exclusion medium, and having a gravity-based flow rate of separation of less than about 10 minutes to produce an eluted solution comprising isolated nucleic acid; and c) collecting the eluted solution for further amplification or analysis.

The present invention further provides a method of purifying a nucleic acid from a biological sample, comprising the steps of: a) subjecting a volume of a mixture of biological sample containing nucleic acid and a lysis agent to size-exclusion chromatography in a column comprising a volume of size-exclusion medium, wherein said volume of the mixture is 0.01 to 0.6 of the volume of the size-exclusion medium, and having a gravity-based flow rate of separation of less than about 10 minutes to produce an eluted solution comprising isolated nucleic acid; and b) collecting the eluted solution for further amplification or analysis.

In practice, the method may be further modified by the use of positive or negative pressure on the column. Positive pressure can be applied to the loading end (top) of the column or negative pressure can be applied to the eluting end (bottom) of the column. When a pressure gradient is employed, optionally the volume of lysis mixture can be 0.35 to 0.8 of the volume of the size-exclusion medium.

In certain embodiments, the volume of the lysis mixture can vary somewhat from between 0.01 to 0.6 of the volume of the size-exclusion medium, to between 0.02 to 0.5 of the volume of the size-exclusion medium, to between 0.1 to 0.4 of the volume of the size-exclusion medium. In certain embodiments, the volume of the lysis mixture is 200-400 µl of sample per 800-1200 µl of filtration medium.

In certain embodiments, the invention provides a gravity-based flow rate of separation of less than 10 minutes to produce an eluted solution comprising isolated nucleic acid, however, the rate can be less than 20 minutes, less than 15 minutes or less than 12.5 minutes, and alternatively can be even less than 10 minutes at less than 9, 8, 7, 6, or 5 minutes.

In certain embodiments, the invention provides further equilibrating said chromatography column with an equilibrating buffer comprising 1-10 mM $Mg^{2+}$ or a non-ionic detergent, or a combination, prior to the subjecting step that essentially will be used for conducting the nucleic acid amplification step.

In certain embodiments, the invention provides that the size-exclusion medium comprises a polymer such as polyacrylamide, polybisacrylamide or polymethacrylamide. In certain embodiments, the invention provides that the size-exclusion medium has a molecular size exclusion limit of about 10 kDa or more. In certain embodiments, the flow rate of separation is gravity-based.

The invention provides that the nucleic acid is either DNA, RNA, or a mixture thereof. The invention further provides that the amplifying step can be selected from the group consisting of RT-PCR, qPCR, digital PCR, LAMP, sequencing, and an enzyme-catalyzed reaction now known or later developed. In certain embodiments, the invention provides that the biological sample can be selected from any source, including blood, saliva, stool, urine, respiratory sample, or enriched culture broth.

In certain embodiments, the biological sample is mixed with a lysis buffer, which causes disruption of cells or virus and releases the nucleic acids. The lysis buffer used in the inventive method comprises alkali hydroxide, such as NaOH or other alkalis, with a pH more than 11, in combination with a detergent, such as sodium dodecyl sulfate (SDS). Alternatively, the lysis buffer can also comprise urea (for example 8M) or a chaotropic salt, such as 6M guanidinium salt. In certain embodiments, the invention provides that the lysis buffer separates double stranded nucleic acid into single stranded nucleic acid and inhibits nucleic acid interactions with protein.

The present invention further provides that the biological sample lysed with the lysis buffer is applied on the top of the SEC gel filtration medium column and is allowed to enter the SEC separating gel by gravity flow. After the sample solution enters the gel medium completely, an additional volume of an elution buffer can be applied on the top of the SEC gel filtration medium and eluted solution in the last flow through is collected. In certain embodiments, the elution buffer is molecular grade water. In certain situations, it is advantageous to use water to move nucleic acids through SEC gel filtration medium with a higher flow rate.

In certain other embodiments, the equilibration and elution buffer is a reaction buffer that is used for a subsequent downstream reaction and/or application, including, but not limited to, DNA/RNA detection and quantitation by various amplification and detection methods, such as RT-PCR, qPCR, digital PCR, LAMP, sequencing, and any other enzyme-catalyzed reactions. In certain other embodiments, the elution buffer can be the same as the equilibrating buffer, the separation buffer, and/or the reaction buffer. In certain other embodiments, the elution buffer is different from the equilibrating buffer, the separation buffer, and/or the reaction buffer.

The present invention provides that because in certain embodiments the equilibration buffer used in the inventive method is substantially free from a nucleic acid amplification inhibitor (such as endogenous protein or exogenous ethanol, or salts such as guanadine chloride) that would interfere with nucleic acid amplification and/or other downstream applications, the purified nucleic acids obtained from the inventive method can be used for various downstream applications discussed above. In certain embodiments, the present invention provides that the elution buffer is substantially free from a nucleic acid amplification inhibitor.

A particular advantage of the inventive method is the ability to rapidly obtain higher volumes of the purified nucleic acid in the amplification reaction, thus, increasing the sensitivity of detection, which is important for diagnostic applications. The volume of eluted nucleic acid material can be used in combination with a lyophilized pellet containing DNA polymerase, dNTPs, and other components required for amplification reaction.

The present invention further provides that in certain embodiments the lysis buffer combined with the biological sample can contain a denaturing agent to cause separation of double-stranded DNA, resulting in single-stranded DNA during the purification process. The examples of such agents include, but are not limited to alkaline buffer at pH above 11 (0.01 M NaOH), guanidinium salts (for example 6 M Guanidinium chloride), urea (for example 8 M urea), and aqueous solutions of organic solvents (such as formamide, dimethylformamide, or dimethylsulfoxide).

The inventive method thus provides purified nucleic acids which can be used directly in the downstream nucleic acid amplification methods without involving a DNA heat denaturation step and additional equipment related thereto (such as a heating block, or an instrument required to reach DNA-denaturation temperature (usually 80-98° C.), providing an advantage that is particularly important for any isothermal amplification technologies, including, but not limited to, loop mediated amplification (LAMP), helicase dependent amplification (HAD), recombinase amplification (RPA). In addition, separation of the strands of DNA may result in change of the molecular shape of nucleic acid molecules increasing apparent hydrodynamic size. This effect may further limit the possibility of DNA entrance into the pores of separating particles and increase DNA mobility in size exclusion chromatography.

As used herein, "nucleic acids" refer to DNA, RNA or any naturally occurring or synthetic modification thereof, and combinations thereof. In certain embodiments, the nucleic acids are DNA, which can be single, double or triple stranded or in any other form, linear or circular. Nucleic acids that can be purified by the method of current invention are polymers with minimal length of 10 bases and no limit on the maximal length. Particularly preferred for isolation and detection in the present invention is genomic DNA.

As used herein "isolated" means that a compound, such as a nucleic acid, is separated from at least some of the constituents with which it is associated in nature. "Isolated" and "purified" may be used interchangeably herein.

As used herein, "biological samples" can be obtained from materials from clinical samples for diagnosis, foods and allied products, and environmental samples. In certain embodiments, such biological samples can comprise all types of mammalian and non-mammalian animal cells, plant cells and bacteria. Representative samples include whole blood and blood-derived products, such as plasma or buffy coat, saliva, semen, tissue homogenates, urine, stool (feces), cerebrospinal fluid or any other body fluids, tissues, cell cultures, cell suspensions, etc. Biological material also includes environmental samples such as soil, water, or food samples. The sample may also include relatively pure or partially purified starting materials, such as semi-pure preparations obtained by other cell separation processes.

As used herein, "lysis buffer" refers to a buffered aqueous solution, which breaks a cell wall or viral capsid, denatures cellular or viral proteins and releases nucleic acids into said solution. In certain embodiments, the lysis buffer includes sodium hydroxide (NaOH) and sodium dodecylsulfate (SDS). In certain embodiments, the lysis buffer comprises 0.01 to 2 M NaOH and 0.1 to 3% SDS. Alternatively, lysis buffer can contain chaotropic salts (for example, Guanidine chloride), protein denaturants (for example urea), buffers with extreme pH (more than 11) and detergents. In certain embodiments, the lysis buffer may contain a nonionic surfactant. The present invention contemplates or combination any suitable surfactant that is determined by empirical selection and evaluation, which is capable of lysing the cell membrane. Methods of lysing cell using a lysis solution are well known in the art and widely described in the literature. As mentioned above, some embodiments of the lysis buffer can simultaneously cause lysis of the cells or disruption of viral capsid and cause denaturation of nucleic acids and separation of DNA strands. The lysis buffer can be provided as a single solution or as separate solutions (for example of alkali and detergent) which combined produce lysis condition.

Conveniently, cell lysis can be achieved by using a lysis buffer comprising chaotropes and/or detergents. For example, the combination of a chaotrope with a detergent is found to be particularly effective. An exemplary suitable lysis solution includes a chaotrope, such as GTC or GHCl and a detergent, such as SDS or Sarkosyl. The lysis agents are supplied in a simple aqueous solution, or included in a buffer solution, to form a so-called "lysis buffer". Any suitable buffer can be used, including for example TRIS, BICINE, TRICINE and phosphate buffers. Alternatively, the lysis agents are added separately. Suitable concentrations and amounts of lysis agents vary according to the precise system and can be appropriately determined.

As used herein, an "elution buffer" refers to a solution that facilitates flow through a size-exclusion media column, and can include the same composition as equilibrating buffer. In the context of the size-exclusion chromatography, it is understood that the main purpose of the elution buffer is to facilitate flow through the column, and the elution buffer, if different from the equilibration buffer, will reach the column exit only after nucleic acids from the biological sample. In some embodiments the elution buffer is a low viscosity solution at a pH which will not cause the chemical decomposition of SEC medium. In some embodiments the elution buffer is water. The elution buffer solution composition may include a dye (for example Phenol Red dye) for easy visual identification of the elution buffer.

As used herein, a "reaction buffer" refers to a buffered solution that facilitates downstream amplification and detection, and can include salts providing buffering capacity in the range of pH optimal to conduct downstream amplification (examples include, but are not limited to TRIS, BICINE, TRICINE), salts facilitating or essential for downstream amplification reaction (such as $Mg^{2+}$ ions), salts creating optimal ionic strength to conduct downstream amplification (including but not limited to NaCl, KCl), detergents (such as TWEEN 20, TRITON X-100, etc) and potentially other compounds which may increase performance of the downstream nucleic acid amplification reaction. Some embodiments of the reaction buffer composition are represented in the Examples section.

As used herein, a "equilibration buffer" refers to a buffered solution for packing SEC medium into a separating column of the present invention. The composition of the "equilibration buffer" can be the same composition as of the reaction buffer. In other embodiments the composition of equilibration buffer is a buffered solution providing stable storage of the purified nucleic acid. The composition of the equilibration buffer in such embodiments comprises buffering compound (examples include, but are not limited to TRIS, BICINE, TRICINE) at pH within the range of pH 6-10. The composition of the equilibration buffer in such embodiment can also include a metal-chelating compound (for example EDTA) protecting nucleic acids from metal-mediated decomposition or hydrolysis. The composition of the equilibration buffer in such embodiments can also include a detergent (such as TWEEN 20, TRITON X-100, etc) to prevent non-specific interaction of nucleic acid to the SEC matrix. The composition of the equilibration buffer can also include a carrier nucleic acid (such as yeast tRNA at 0.1 to 10 µg/ml, polyA-polyT polymers, etc.) to prevent non-specific interaction of nucleic acid to SEC matrix. The composition of the equilibration buffer can also include inhibitors of bacterial growth or disinfectants (for example sodium azide) to enable ambient storage of packaged columns.

The present invention further provides that the biological sample lysed with the lysis buffer is applied on the top of the SEC gel filtration medium column and is allowed to enter the SEC separating gel by gravity flow. The preferred scheme of the process of this embodiment is presented in FIG. 1. In certain embodiments, the SEC gel filtration medium column is equilibrated in equilibrating buffer. In certain other embodiments, the SEC gel filtration medium column is equilibrated in a reaction buffer for downstream analysis (for example amplification). In certain other embodiments, the biological sample lysed with the lysis buffer is applied directly to the column without removing any of the components in an intervening step between lysis and column application.

Gel filtration or size exclusion chromatography is a method in which molecules in solution are separated by their size. Small molecules that can penetrate pores of the stationary phase can enter the entire pore volume and the interparticle volume, and will elute late. A very large molecule (such as a nucleic acid) that cannot penetrate the pores moves in the interparticle volume (~30-35% of the column volume) and will elute earlier when this volume of mobile phase has passed through the column. The underlying principle of SEC is that particles of different sizes will elute (filter) through a stationary phase at different rates. A preferred mode of gel filtration chromatography of the present invention is using gravity flow, however, certain vacuum or pressure modifications can be made to modify the flow rate as described below.

Gel filtration medium is a stationary phase for gel filtration chromatography. Particularly used for practicing of the present invention are gel filtration mediums, which have pores small enough to prevent nucleic acids from entering the pores, but large enough to allow pore entrance by protein molecules, or other organic (such as carbohydrates, lipids, etc) and inorganic compounds and have minimal interaction with the surface of the stationary phases. In certain embodiments, the SEC gel filtration chromatography column has molecular size exclusion limit of about 10 kDa or more. More preferably, the SEC gel filtration mediums of present invention include stationary phases which exclude molecules with molecular weight more than $5 \times 10^6$ Da, while providing separation of molecules with molecular weight in the range of 50,000 to 500,000 Da. The examples of gel filtration medium useful for the present invention include, but are not limited to: Sephacryls (S100, S200, S300, S400, S500, S1000), Sepharoses (2B, 4B and 6), Toyopearls (HW-50, HW-55, HW-65, HW-75). In certain other embodiments, the Sephacryl gel filtration medium has a particle size of about 50 micrometers.

In certain embodiments, the SEC gel filtration medium is packed into a disposable plastic column containing a porous filter at the bottom. The SEC gel filtration medium is covered by another porous filter and column can be capped at the top to prevent evaporation for a long-term storage. In certain embodiments, the design of the device utilizing the inventive method may include a removable adsorbent pad, which can retain the liquid coming from the SEC gel column during the sample application. In certain other embodiments, the SEC gel-filtration medium is enclosed between lower and upper porous filter disks having a porosity of about 40-100 micrometers.

After the sample solution enters the gel medium completely, a volume of an elution buffer is applied on the top of the SEC gel filtration medium to facilitate flow through the column. Optionally, an additional volume of the elution buffer is applied to provide more flow through the column. The volumes of the column, the sample and the elution buffer can be selected to provide the best separation with minimal dilution of applied nucleic acids. Several examples of such ratios are presented in the Examples. The volume displaced by the last volume of the elution buffer is collected. Since the buffer applied to the SEC column after the sample will always exit the column after the nucleic acids from the sample, it's composition is determined mostly by convenience factors. In certain embodiments, the elution buffer is molecular grade water. It is advantageous to use water to move nucleic acids through a SEC gel filtration medium with a higher flow rate. In certain other embodiments, the elution buffer can be the same as the equilibrating buffer, the separation buffer, and/or the reaction buffer. In certain other embodiments, the elution buffer is different from the equilibrating buffer, the separation buffer, and/or the reaction buffer.

Figure 2:
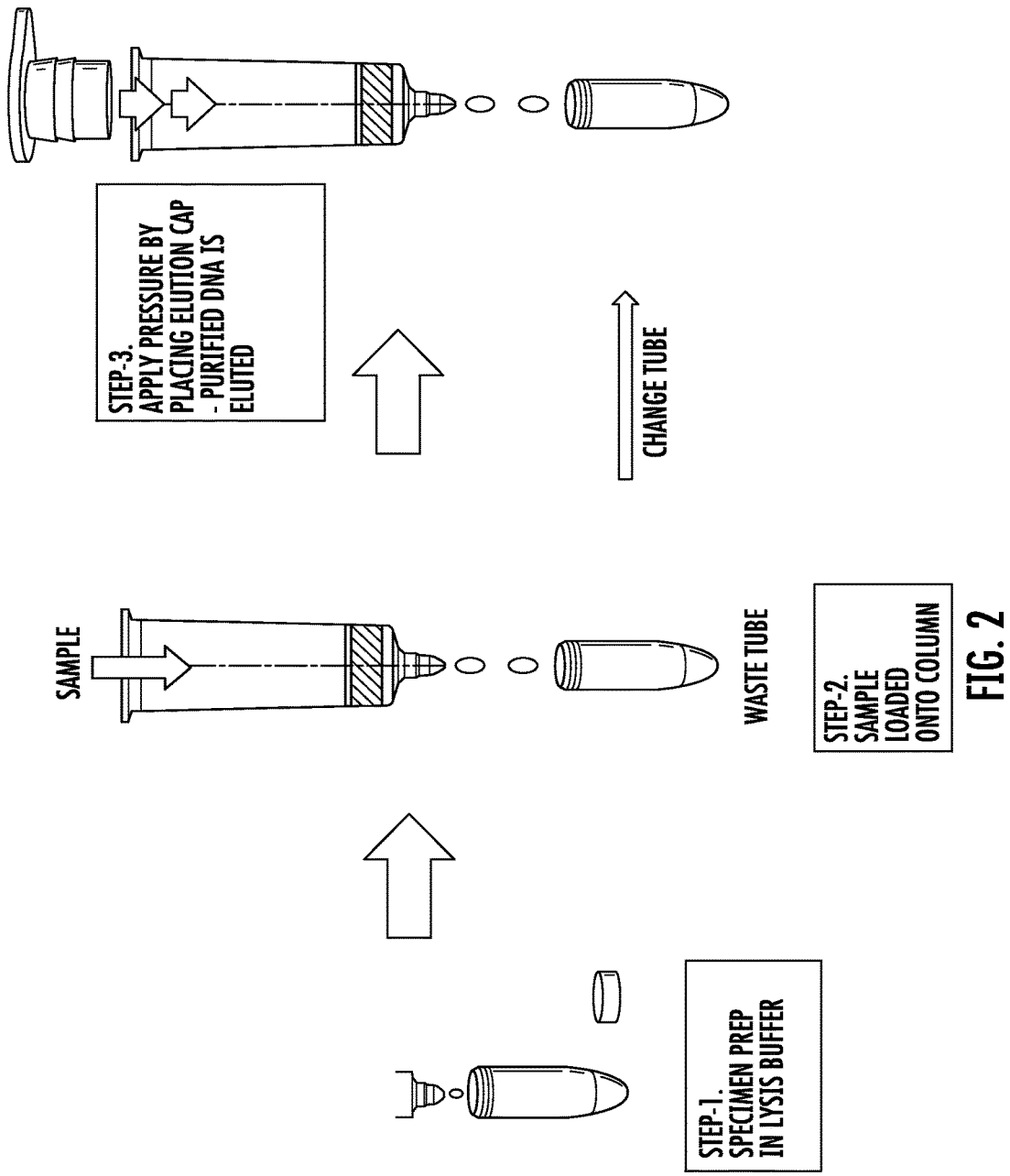
FIG. 2 illustrates a universal sample preparation (USP) workflow scheme using positive pressure.

In an alternative embodiment of the invention, a lysis mixture is applied on the column and is allowed to enter the separation medium. A positive pressure differential is applied to the column to produce an eluted solution containing nucleic acid. The eluted solution containing nucleic acid is collected for subsequent amplification or analysis. In certain embodiments, positive pressure forces interstitial fluid from the SEC column, thereby destroying the SEC column. In certain embodiments as depicted in FIG. 2, the pressure differential is created by applying a positive pressure to the loading side of the column. The optimal ratio of the volume of lysis mixture to the volume of the column is defined by two main factors: first the volume of the lysis mixture should be larger than void volume of the column, and second, the volume of the lysis mixture should be less than the volume at which components of the lysis buffer would elute from the column under constant flow conditions (without applying additional pressure). In one embodiment, the volume of the lysis mixture is in the range more than 0.35 volume of the SEC column and less than 0.8 volume of the SEC column (the volume of SEC volume is defined as the volume of SEC medium packed into a column). In another preferred embodiment, the volume of the lysis mixture is in the range of more than 0.4 volume of the SEC column and less than 0.6 volume of the SEC column. In some embodiments of this invention, the lysis mixture enters the column under gravity flow. Under gravity flow conditions, flow spontaneously stops when the lysis mixture enters the column preventing the column from draining.

The positive pressure differential can be provided by different means, including, but not limited to, by means of inserting a plunger or a pressurizing cap into a barrel of the SEC column. The volume of the solution eluted from the column is typically less than the expected void volume of the SEC column. In the preferred embodiment this volume is in the range of 0.15-0.3 volume of the SEC column, and more preferably in the range of 0.175-0.25 volume of the SEC column.

Notably, the volume of collected liquid containing nucleic acids is less than the volume of the applied lysis mixture. By optimizing ratios of volume of SEC column, volume of lysis mixture and volume of drained liquid, it is conceivable to achieve conditions, under which nucleic acids are not diluted during said SEC purification.

Moreover, if the leading front of the nucleic acid band migrating through the column is slowed during migration due to interaction with SEC medium (for example interaction of electrostatic nature), is may be possible to obtain an effective concentration of nucleic acid in the collected fraction.

Figure 3:
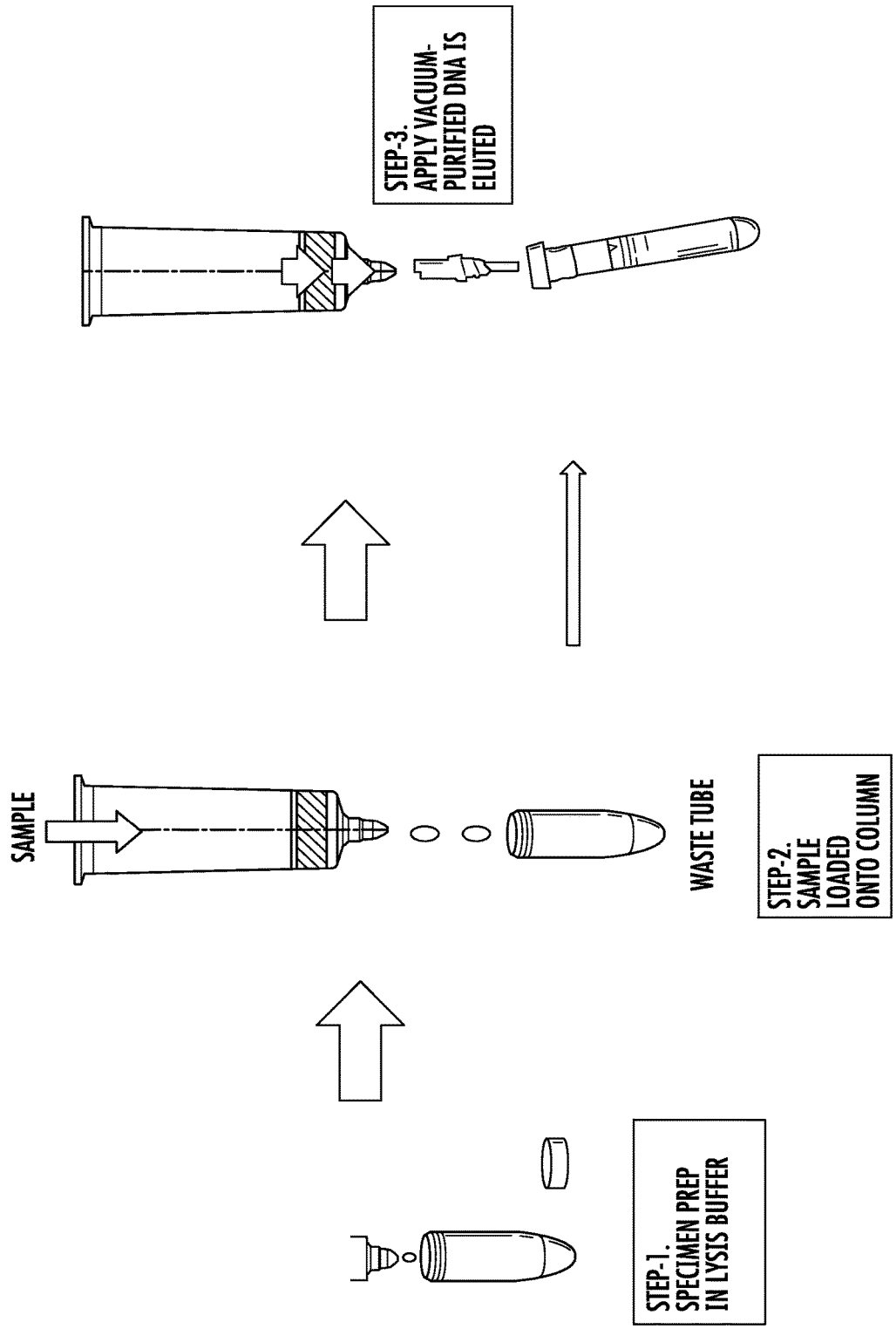
FIG. 3 illustrates a universal sample preparation (USP) workflow scheme using negative pressure.

In another alternative embodiment of the invention (depicted in FIG. 3), a sample containing nucleic acids is applied on the column and is allowed to enter the separation medium. A negative pressure or vacuum is applied to the eluting or exit side of the column forcing interstitial fluid containing nucleic acid to exit the column. The eluted fluid containing nucleic acid is collected for further amplification or analysis.

In certain embodiments, the ratio of the volume of the sample to the SEC medium volume should be less than 1.0, and can be in a range of 0.01 to 0.9. Optionally, an additional volume of buffer could be applied to the column to move nucleic acids toward the exit side of the column. The volume of the additional buffer is typically less than the volume of the SEC medium in the column.

In some embodiments of this invention, the nucleic acid sample enters the column under gravity flow. Under conditions of gravity flow, the flow will spontaneously stop when the sample has entered the SEC medium preventing the column from draining.

The negative pressure differential or vacuum can be provided by different means, including, but not limited to, by means connecting a tube (for example a Vacutainer tube) under a low pressure to the exit side of the SEC column. The volume of the interstitial liquid drained from the column is typically less than the expected void volume of the SEC column. In the preferred embodiment, this volume is in the range of 0.1-0.4 volume of the SEC column, and in some embodiments in the range of 0.175-0.25 volume of the SEC column.

The negative pressure differential is the difference in the pressure between pressure to which the SEC medium and eluting end of the column are exposed. For example, if the SEC medium is under atmospheric pressure conditions, the pressure applied to the eluting end of the column is less than atmospheric pressure.

Notably, the volume of collected liquid containing nucleic acids can be less than the volume of the applied sample containing nucleic acids. By optimizing ratios of volume of SEC column, the volume of lysis mixture and the volume of drained liquid, it is possible to achieve conditions under which nucleic acids are not diluted during said SEC purification.

Moreover, if the leading front of the nucleic acid band migrating through the column is slowed during migration due to interaction with SEC medium (for example electrostatic interaction), it is possible to obtain an effective concentration of nucleic acid in the collected fraction.

The alternative methods provide even faster separation, being limited only by the time required for the lysis mixture to enter the column bed formed by SEC medium.

In certain other embodiments, the equilibration buffer, in which nucleic acids are eluted, is a reaction buffer that is used for a subsequent downstream reaction and/or application, including, but not limited to, DNA/RNA detection and quantitation by various amplification and detection methods, such as RT-PCR, qPCR, digital PCR, LAMP, sequencing, and any other enzyme-catalyzed reactions. The equilibration buffer used in the present inventive method can be substantially free from an inhibitor that would interfere with nucleic acid amplification and/or other downstream applications.

A particular advantage of the inventive method is the ability to obtain a larger volume of the purified nucleic acid for use in the amplification reaction, thus, increasing the sensitivity of detection, which is particularly important for diagnostic applications. The largest volume of eluted material can be used in combination with a lyophilized pellet containing DNA polymerase, dNTPs, and other component required for amplification reaction. As used herein, the "DNA polymerase" is any enzyme that catalyzes or helps to catalyze polymerization of deoxyribonucleotides into a DNA strand using a nucleic acid (DNA or RNA) template. DNA polymerase of present invention can be represented by a mixture of enzymes with a DNA polymerase activity.

The present inventive method thus provides purified nucleic acids to be used directly in the downstream nucleic acid amplification methods without involving a DNA heat denaturation step and additional equipment related thereto, such as a heating block instrument required to reach DNA-denaturation temperature (usually 80-98° C.), providing an advantage that is particularly important for isothermal amplification technologies, including, but not limited to, loop mediated amplification (LAMP), helicase dependent amplification (HAD), recombinase amplification (RPA). As used herein, the "nucleic acid amplification" is the process of increasing copy number of the original nucleic acid sequence (DNA or RNA) using enzyme or enzymes catalyzing polynucleotide synthesis. The examples of nucleic acid amplifications of current invention include, but are not limited to, polymerase chain reaction (PCR), loop-mediated amplification (LAMP), template-mediated amplification (TMA).

The present invention further provides a kit for purifying nucleic acid from a biological sample. In other embodiments a kit is provided for detecting a nucleic acid present in a biological sample. In certain embodiments, purification and detection kits may include one or more of the following as herein described: a lysis buffer; a size exclusion chromatography column; the components for constructing a size exclusion chromatography column; tubes for specimen, waste and/or sample collection; equilibration buffer. Instructions for using the kits for nucleic acid purification and/or detection according to the methods of the present invention are preferably provided therewith.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of the preferred embodiments thereof and from the claims. These and many other variations and embodiments of the invention will be apparent to one of skill in the art upon a review of the appended description and examples.

EXAMPLES

Example 1

Preparation of Separation Columns and USP Device

The USP device of the present example contains a plastic column containing Sephacryl gel-filtration medium enclosed between lower and upper porous filter disks. Gel volumes in a range of 0.83-1.32 ml were evaluated. A large number of columns with a volume of SEC medium of 0.89 ml and 1.14 ml were prepared. Target tolerance for gel volume+/−3%. The USP device was permanently closed at the bottom prior to use. The user opened the fluid path to initiate operation (by snapping off or cutting lower tip of the column).

Fill procedure: A lower disk was introduced in the present inventive universal sample preparation (USP) device, and then suspension of the Sephacryl gel (particle size 50 μm) filtration medium in Illumigene reaction buffer was dispensed and/or packed into the device. The concentration of suspension was 40-60%, with 55% most frequently used. An upper disk was also introduced in the device (40-100 μm porosity of the filter disk allows buffer to go through the filter, while locking gel particles between two filters) to cover the Sephacryl gel filtration medium. The USP Device was capped at the top to avoid evaporation. The USP device with the Sephracryl gel filtration medium column can be stored at 2-27° C. for prolonged periods of time (e.g., up to a year). The USP device may include a removable adsorbent pad, which can retain the liquid coming from the column during the sample application.

Example 2

Viral RNA and Detection of Viruses

The Purpose of this experiment was to demonstrate the ability of Universal Sample Preparation (USP) workflow to purify viral RNA and the ability of Universal Sample Prep (USP) workflow to detect viral nucleic acid. This experiment was done with one-step RT reaction and amplification. The nasopharyngeal and nasal clinical specimens were collected in transport medium. The medium was frozen at −80° C., until use. 200 ul of clinical specimen was transport to a clean Eppendorf's tube. 50 µl of lysis buffer [0.2 N NaOH and 1% SDS) and 50 µl of PBS buffer supplemented with azide (PBSA) was added to same tube. The tube was inverted 3 times to mix. 200 µl of specimen mix was loaded onto USP columns (equilibrated in LAMP reaction buffer {Trizma Base 4.8456 gm/ltr., KCl 1.4912 gm/ltr., Magnesium Sulfate, 2.5 M (anhydrous) 6.4 ml/ltr., Ammonium Sulfate 2.6426 gm/ltr., Tween-20 2.0 ml/ltr., Sodium Azide 0.94 gm/ltr}).

Once specimen entered the gel, 200 ul of molecular grade water was loaded on top of column. A clean elution tube was placed for the final step. 200 ul of reaction buffer was added to the column and eluted material was collected. 5 ul of elution was used to perform one step RT-LAMP at 55° C. The reaction was read in real time on a Rotorgene Q real-time PCR thermocycler.

Composition of Florescent LAMP Reaction—
Flu a Florescent LAMP Reaction Composition

| | |
|---|---|
| dNTP's | 1.4 mM |
| 10% BSA, | 0.6% |
| FluA1 F3 primer | 0.2 uM |
| FluA1 B3 primer | 0.2 uM |
| Flu AMFIP primer | 1.6 uM |
| FluA1 BIP primer | 1.6 uM |
| FluA1 LF primer | 0.8 uM |
| FAM FluA1 LB primer | 0.5 uM |
| BST polymerase, | 0.9 ul |
| Reverse Transcriptase | 1 U |
| RNAse inhibitor (40 U/ul) | 10 U |

Flu B Florescent LAMP Reaction Composition

| | |
|---|---|
| dNTP's | 1.4 mM |
| 10% BSA, | 0.6% |
| FluB1 F3 primer | 0.2 uM |
| FluB1 B3 primer | 0.2 uM |
| FluB1FIP primer | 1.6 uM |
| FluB1 BIP primer | 1.6 uM |
| FluB1 LF primer | 0.8 uM |
| FB LBQ | 0.04 uM |
| BST polymerase, | 0.9 ul |
| Reverse Transcriptase | 1 U |
| RNAse inhibitor (40 U/ul) | 10 U |

Flu A Specimen

| Specimen ID | ct value | Detection |
|---|---|---|
| PSH 1964 | 18.01 | Positive |
| PSH 0337 | 34.33 | Positive |
| PSH 1965 | 17.45 | Positive |
| PSH 1927 | 18.77 | Positive |
| PSH 1979 | 18.42 | Positive |

Flu B Specimen

| Specimen ID | ct value | Detection |
|---|---|---|
| PCMC 9410 | 20.76 | Positive |
| PCMC 4483 | 17.63 | Positive |
| PCMC 11207 | 14.38 | Positive |
| PCMC 10457 | 15.32 | Positive |
| PCMC 11383 | 29.9 | Positive |

Influenza Negative Specimen

| Specimen ID | ct value | Detection |
|---|---|---|
| 7678 | 0 | Negative |
| 7679 | 0 | Negative |
| 7711 | 0 | Negative |
| 7756 | 0 | Negative |
| 7757 | 0 | Negative |

Example 3

Bacterial DNA and Detection in Stool Specimen

This experiment was performed to demonstrate the ability of Universal Sample Prep workflow to lyse bacterial cells and to obtain purified DNA. This experiment also demonstrates that USP workflow purifies DNA from clinical stool specimen that is solid, semi-solid and water. The purified DNA is ready for downstream molecular applications.

Illumigene C. diff positive stool specimens were obtained from clinical sites. The specimens were kept frozen at −80° C., until use. Consistency of stool specimens was observed to be solid, semi-solid and water.

A full swab load of specimen was treated with 1480 ul lysis buffer {0.1N NaOH and 0.54% SDS}. 50 ul of Assay control, containing E. coli transformed with a plasmid encoding Spa gene of Staphylococcus aureus. (Formaldehye fixed E. coli cells were suspended in 10 mM Tris 0.1 mM EDTA at Absorbance 600 nm of 0.700-0.800. The cell suspension was diluted 1:10,000 in PBSA with 400 ng/ml yeast tRNA was added to the sample. Lysed sample was vortexed to mix for 10 seconds and filtered through 7 µm filter.

200 µl of lysis mix was loaded onto USP columns made with SEPHACRYLA S-300 and equilibrated in LAMP reaction buffer (composition described above). Once specimen entered the gel, 200 µl of molecular grade water was loaded on top of the column. Once molecular grade water entered into gel completely, the waste tube was removed from under the column. A clean elution tube was placed for the final step. 200 µl of molecular grade water was added to the column and last flow through was collected in clean elution tube. 50 µl of elution was used to amplify toxin A gene of C. diff in LAMP reaction at 63° C. using Meridian C. difficile test device (Catalog #280050). 50 µl of elution was use to amplify spa gene of S. aureus in LAMP reaction at 63° C.

Results of the amplification test are presented in a table below:

| Specimen Consistency | Specimen ID | Test (min) | Control (min) |
|---|---|---|---|
| Solid | #17 | 24 | 24 |
| Solid | #14 | 27 | 24 |
| Solid | #36 | 28 | 28 |
| Semi-Solid | #48 | 26 | 23 |
| Semi-Solid | #42 | 22 | 25 |
| Watery | #19 | 23 | 27 |
| Solid | #17 | 24 | 24 |

Example 4

Urine Specimen

Columns were packed with 1.14 ml of Sephacryl 5300 SEC medium equilibrated in LAMP reaction buffer supplemented with yeast tRNA as carrier. Leftover clinical urine samples, previously tested for *Chlamydia* and Gonorrhea using nucleic acid amplification test (ProbeTec (Beckton Dickinson)) were processed through USP separation.
a) Urine Specimen Preparation
1.5 mL of urine was transferred into a clean 2.0 mL micro centrifuge tube and supplemented with a drop of Assay control (diluted suspension of *E. coli* cells, harboring a plasmid comprising sequence of Spa gene of *Staphylococcus aureus*, dispensed from a dropper bottle. The tubes were centrifuged at 6000 rpm for 3 min. The supernatants were discarded by inverting tubes. Pellets containing cells were resuspended in 250 µL of lysis buffer (0.2 N NaOH and 1% SDS).
b) DNA Processing
250 µL of lysis mixture was applied to the USP column and liquid was allowed to enter the column medium by gravity flow. 250 uL of buffer (containing Red dye to enhance visual tracking of liquid flow through the top column filter) was applied to the column and liquid was allowed to enter the column medium by gravity flow. 250 µL of elution buffer was applied to the column and displaced buffer eluted from the column was collected into a clean 2.0 mL micro centrifuge tube.
c) LAMP Amplification:
50 µL of processed DNA sample were added to the TEST and to the Control chambers of Illumigene devices (Meridian Bioscience, Cincinnati, Ohio) containing lyophilized beads comprising dried LAMP amplification reagents. A drop of Mineral oil was added to each chamber to overlay reaction mixture. Illumigene devices were closed and placed into illumiPro reader for 40 minute incubation at 63° C. Optical signal was measured by the reader at the beginning, during, and at the end of incubation. 55 out of 55 clinical urine samples positive for *Chlamydia trahomatis* by BD ProbeTec were positive by LAMP amplification after processing through USP. 13 out of 14 clinical urine samples positive for *Neisseria gonorrhea* by BD ProbeTec were positive by LAMP amplification after processing through USP. Average time to positivity in test LAMP reactions was 20 minutes.

Example 5

Transport Media

The purpose of this experiment was to demonstrate the feasibility of using Universal Sample Preparation workflow to lyse cells and purify DNA from specimens that are collected in Transport medium.

For this purpose, Purified *Mycoplasma* stock culture was spiked into M4 Transport medium at 100 CFU/ml and 50 CFU/ml.

300 ul of *Mycoplasma* sample was transferred to a clean tube. 50 µl of assay control and 50 µl of lysis buffer was added. The mixture was inverted three times to mix. 350 ul of sample mixture was loaded onto USP columns. The flow-through is collected in a waste tube. Once the sample entered the column completely, the waste tube was removed. A clean tube is placed under the column. 350 µl of reaction buffer was added onto the column. The flow through with purified DNA is collected in the clean tube.

50 µl of eluant is loaded into the test side of *Mycoplasma* test devices to amplify *Mycoplasma* specific sequence. 50 µl of eluant is loaded into the control side of *Mycoplasma* test device to amplify spa specific sequence.

| Mycoplasma | Time for Amplification | | |
|---|---|---|---|
| CFU/ml | Test Avg | StdDev | Detection |
| 100 | 20.6 | 1.26 | Positive |
| 50 | 20 | 0 | Positive |

Example 6

Bronchoalveolar Lavage

This example presents evidence for Bronchoalveolar Lavage to be a suitable clinical specimen for *Mycoplasma* DNA purification and amplification with Universal Sample Prep workflow.

For this purpose appropriate dilution of *Mycoplasma* stock culture was prepared in clinical matrix. The dilutions were 150 CFU/ml and 75 CFU/ml.

200 ul of above dilutions was mixed with 50 µl of lysis buffer and 50 ul of assay control. Tube was inverted three times to mix. 200 µl of lysate was loaded onto USP column. Once the entire sample entered the column, 200 µl of molecular grade water was loaded onto column. After collecting last drop of flow through, the waste tube was discarded. A clean elution tube was placed under USP column. 200 µl of LAMP reaction buffer was added to the column. The flow through was collected. 50 ul of elution was added to *Mycoplasma* test device to test for presence of *Mycoplasma* DNA. 50 ul of elution was added to control side of test device to test the presence of control DNA

| Samples | Test | Control |
|---|---|---|
| 5 cfu/test FH Strain | 1 at 23 min., 7 at 25 min., | 7 at 27 min., |
| Mycoplasma pnuemoniae | 1 at 30 min., 1 at 37 min., | 3 at 30 min. |
| 2.5 cfu/test FH Strain | 2 at 23 min., 5 at 25 min., | 3 at 27 min., |
| Mycoplasma pnuemoniae | 3 at 27 min. | 7 at 30 min. |

Example 7

Blood Culture

This experiment was performed to demonstrate the feasibility of amplifying DNA from blood and blood-related products with USP workflow.

A blood culture that had been shown to be positive for *Staphylococcus aureus* was tested using USP procedure. 400 ul of positive blood culture was mixed with 100 μl of lysis buffer. The tube was inverted three times to mix. 200 μl of lysate was loaded onto USP column. 200 ul of 1× reaction buffer was added to column followed by 200 ul of molecular grade water for elution.

| # | Specimen | Time for Spa amplification (min) | Detection |
|---|---|---|---|
| 1 | Blood culture | 23 | Positive |
| 2 | Blood culture | 20 | Positive |

Example 8

Use of Sephacryl 5-1000

The purpose of this experiment was to demonstrate the feasibility of using Universal Sample Preparation workflow to lyse cells and purify DNA from specimens that are collected in Transport medium.

For this purpose, Purified *Mycoplasma* stock culture was spiked into M4 Transport medium at 20 CFU/ml.

300 μl of *Mycoplasma* sample was transferred to a clean tube. 50 ul of assay control and 50 μl of lysis buffer was added. The mixture was inverted three times to mix. 350 ul of sample mixture was loaded onto USP columns. The flow-through is collected in a waste tube. Once the sample entered the column completely, the waste tube was removed. A clean tube is placed under the column. 350 μl of reaction buffer was added onto the column. The flow through with purified DNA is collected in the clean tube.

50 μl of eluant was loaded into the test side of *Mycoplasma* test devices to amplify *Mycoplasma* specific sequence. 50 ul of eluant was loaded into the control side of *Mycoplasma* test device to amplify spa specific sequence.

| Myco CFU/ml | Test (min) | Control (min) |
|---|---|---|
| 20 | 27 | 30 |
| 20 | 25 | 30 |
| 20 | 27 | 30 |
| 20 | ND | 27 |
| 20 | 30 | 30 |
| 20 | 30 | 30 |
| 20 | ND | 30 |
| 20 | ND | 30 |
| 20 | 27 | 30 |
| 20 | ND | 30 |

Example 9

Volume Ranges

This study was performed to demonstrate the versatility and flexibility in volumes of sample, wash buffer and elution buffer in USP workflow. Three different volumes of sample, wash and elution buffer each were used in this study. *C. diff* spiked stool was used as sample input and illumigene *C. diff* test was used the detect DNA. *C. diff* spiked stool was diluted in pooled negative stool to a final of 256 CFU/test.

A full swab load of specimen was mixed with 1480 μl lysis buffer. Two drops of *Mycoplasma* Assay control, containing *E. coli* transformed with spa gene from *Staphylococcus aureus* was added to sample. Sample was vortexed to mix for 10 seconds. 10 drops were filtered through 7 μm filter.

160 μl, 200 μl and 240 μl of sample were loaded onto USP columns (made with SEPHACRYL S-300 and equilibrated in LAMP reaction buffer). Once specimen entered the gel, 160 μl, 200 μul and 240 μl of molecular grade water was added. Once molecular grade water entered into gel, completely, the waste tube was removed from under the column. A clean elution tube was placed for the final step. 160 μl, 200 μl and 240 μl of molecular grade water were added to the column and last flow through was collected in clean elution tube. 50 μl of elution was used to amplify toxin A gene of *C. diff* in LAMP reaction at 63° C. 50 ul of elution was use to amplify spa gene of *S. aureus* in LAMP reaction at 63° C.

| Samples Volume | Test | Control |
|---|---|---|
| 160 ul sample onto USP (−20%) | 7 at 27 min., 3 at 30 min. | 10 at 23 min., |
| 200 ul sample onto USP | 5 at 27 min., 5 at 30 min. | 9 at 23 min., 1 at 25 min. |
| 240 ul sample onto USP (+20%) | 3 at 25 min., 3 at 27 min., 3 at 30 min., 1 at 33 min. | 10 at 23 min. |

| Wash Volume | Test | Control |
|---|---|---|
| 160 ul Wash buffer (−20%) | 8 @ 30 min., 1 @ 40 min., 1 ND | 4 @ 23 min., 4 @ 25 min., 2 @ 27 min. |
| Standard work flow | 5 at 27 min., 5 at 30 min. | 9 at 23 min., 1 at 25 min. |
| 240 ul Wash buffer (+20%) | 1 @ 25 min., 6 @ 27 min., 1 @ 30 min., 2ND | 9 @ 23 min., 1 @ 30 min., |

| Elution Volume | Test | Control |
|---|---|---|
| 160 ul Elution (−20%) | 1 @ 25 min., 6 @ 27 min., 2 @ 30 min., 1 @ 40 min., | 8 @ 23 min., 2 @ 25 min., |
| Standard work flow | 5 at 27 min., 5 at 30 min. | 9 at 23 min., 1 at 25 min. |
| 240 ul Elution (+20%) | 1 @ 25 min., 5 @ 27 min., 2 @ 30 min., 1 @ 33 min., 1 @ 35 min., | 10 @ 23 min., |

Example 10

Testing of Volume Tolerances for USP

Determination of input and output volume tolerance of extraction method is an important step in evaluating the efficacy of the method. The following experiment was performed to test the volume tolerances for USP. First columns were packed with 1.78 ml (50% slurry of Sephacryl S 300 hr made in 1× reaction buffer). *Mycoplasma* pneumonia bacterial stock was diluted to 50 cfu/ml concentration in M4 medium and the internal control containing *E. coli* cells harboring plasmid containing Spa gene of *Staphylococcus aureus* was diluted to 10,000 times in PBSA buffer with 400 ng/ml of yeast tRNA. Samples were prepared with varying amounts of internal control, *Mycoplasma* and lysis buffer as shown in the table to achieve the inputs of 250, 300 and 400 ul. Samples were mixed 6 times gently with 200 ul automatic pippet. Prior to the loading of sample to the columns, the excess buffer was drained out. The applied samples were allowed to absorb into the gel material for a minute and the flow thorough was discarded. Following this process, nucleic acid was eluted using various amounts (200, 250, 300 and 400 ul) of 1× reaction buffer. The eluates were collected in clean 1.5 ml tubes for about one minute. Fifty microliters of eluates were applied to Illumigene *Mycoplasma* devices containing test and control beads. These devices were further incubated at 63° C. for 40 min in ILLUMIPRO-10 reader. Table shows that for a range of input and elution volumes, the test and controls DNAs were detected.

| Sample volume (μl) | Control volume (μl) | Lysis solution volume (μl) | Total input volume (μl) | Output volume (μl) (elution) | Test (min) | Control (min) |
|---|---|---|---|---|---|---|
| 100 | 50 | 100 | 250 | 300 | 33 | 37 |
| 200 | 50 | 100 | 400 | 300 | 30 | 33 |
| 150 | 50 | 100 | 300 | 250 | 30 | 33 |
| 100 | 100 | 100 | 300 | 400 | 30 | 33 |
| 100 | 50 | 150 | 300 | 200 | 33 | 33 |
| 200 | 50 | 150 | 400 | 200 | 30 | 33 |

Example 11

Sample Elution with a Syringe Plunger Instead of Gravity

Samples: Liquid Amies medium spiked with *Chlamydia* (CT) and Gonorrhea (NG) cells as shown in the Table 1 below. One ml of the *Chlamydia* and Gonorrhea spiked medium was mixed with approximately 40 μl of assay control and 250 μl of lysis buffer and mixed the contents by simple inversions.

M-Prep Columns: The M-prep columns were packed with 1.14 ml of Sephacryl 5300 hr slurry which is saturated in illumigene reaction buffer. Five hundred micro liters of the lysate loaded to the column and the eluted flow through discarded. The nucleic acid sample was collected in a 1.5 ml tube from the columns with the help of a syringe plunger by simply pushing the plunger inside the column. The eluted nucleic acid volume obtained ranges from approximately 200 to 450 μl.

Illumigene Amplification: Fifty micro liters each of elute added to the illumigene *Chlamydia* test and control reactions and another 50 μl each of elute added to the illumigene Gonorrhea test and control reactions. The loaded reaction devices incubated at 63 C for 40 minutes on ILLUMIPRO-10 readers and collected the amplification timings as shown in Table 1.

TABLE 1

Ten sample replicates tested at each concentration. illumigene amplification detection times are shown in minutes. ND denotes no detection.

| Liquid Amies spiked with CT and NG cells per ml | Sample volume (μl) | Assay control (μl) | Lysis buffer volume (μl) | Column input volume (μl) | Column Output volume (μl) | Elution with plunger | | | |
|---|---|---|---|---|---|---|---|---|---|
| | | | | | | CT | | NG | |
| | | | | | | Test (Time in minutes) | Control (Time in minutes) | Test (Time in minutes) | Control (Time in minutes) |
| 100 cfu/ 10 ifu (n = 10) | 1000 | 40 | 250 | 500 | 200-450 | 9@20, 23 | 6@23, 2@25, 27, 30 | 7@20, 3@23 | 23, 6@25, 2@27, 33 |
| 30 cfu/ 3 ifu (n = 10) | 1000 | 40 | 250 | 500 | 200-450 | 7@20, 3@23 | 4@23, 5@25, 35 | 20, 4@23, 4@25, 30 | 2@23, 7@25, 33 |
| 10cfu/ 1 ifu (n = 10) | 1000 | 40 | 250 | 500 | 200-450 | 2@20, 5@23, 25, 35, ND | 8@23, 2@25 | 20, 6@23, 25, 2@ND | 5@23, 5@25 |

Example 12

Sample Elution with the Sample Prep Device Cap Instead of Gravity Combined with Detection by LAMP and PCR Samples: Previously tested and *Neisseria gonorrhea* positive frozen Urine samples selected for the study. One ml of the Urine sample was mixed with approximately 40 μl of assay control and 80 μl of 1M NaOH followed by 250 μl of lysis buffer and mixed the contents by simple inversions.

M-Prep Columns: The M-prep columns were packed with 1.14 ml of Sephacryl S300 hr slurry which is saturated in illumigene reaction buffer. Five hundred or 700 micro liters of the lysate loaded to the column and the eluted flow through discarded. The nucleic acid sample was collected in a 1.5 ml tube from the columns with the help of the M-prep column cap by simply pushing inside the column. The eluted nucleic acid volume obtained was about 200-250 μl.

Illumigene Amplifications: Fifty micro liters each of elute added to the illumigene Gonorrhea test and control reactions. The loaded reaction devices incubated at 63° C. for 40 minutes on illumiPro-10 readers and collected the amplification timings as shown in Table 2.

Real-Time PCR Amplifications: Five micro liters of the eluted DNA from the each sample prep above mentioned method was used in the PCR reactions. The reactions were setup using Quantifast (Qiagen) master mix and the amplifications performed using Rotor-Gene Q (Qiagen) thermal cycler. The Ct values are shown in table 3. ND denotes that no amplification was noticed for those particular samples

TABLE 2 illumigene amplification detection times are shown in minutes. ND denotes no detection. Multiple time points for a given test shows the repeat test results

| Urine Sample | Sample (μl) | Assay control (μl) | Lysis buffer (μl) | 1M NaOH (μl) | Column input (μl) | Column Output (μl) | 500 μl lysate load in to the column Test Time in minutes | 500 μl lysate load in to the column Control Time in minutes | 700 μl lysate load in to the column Test Time in minutes | 700 μl lysate load in to the column Control Time in minutes |
|---|---|---|---|---|---|---|---|---|---|---|
| 1 | 1000 | 40 | 250 | 80 | 500 | 250 | 23 | 33 | 23 | 23 |
| 2 | 1000 | 40 | 250 | 80 | 500 | 250 | 20 | 37 | 20 | 33 |
| 3 | 1000 | 40 | 250 | 80 | 500 | 250 | ND, 60 | 25, 25 | ND, ND | 25, 30 |
| 4 | 1000 | 40 | 250 | 80 | 500 | 250 | 20 | 27 | 20 | 25 |
| 5 | 1000 | 40 | 250 | 80 | 500 | 250 | 20 | 23 | 20 | 25 |
| 6 | 1000 | 40 | 250 | 80 | 500 | 250 | 27, 35 | 45, 37 | ND, 37 | ND, 33 |
| 7 | 1000 | 40 | 250 | 80 | 500 | 250 | 20 | 23 | 20 | 25 |
| 8 | 1000 | 40 | 250 | 80 | 500 | 250 | 25 | 25 | 20 | 25 |
| 9 | 1000 | 40 | 250 | 80 | 500 | 250 | 20 | 27 | 20 | 27 |
| 10 | 1000 | 40 | 250 | 80 | 500 | 250 | 23 | 33 | 20 | 23 |
| 11 | 1000 | 40 | 250 | 80 | 500 | 250 | 20 | 25 | 20 | 23 |
| 12 | 1000 | 40 | 250 | 80 | 500 | 250 | ND, 20 | ND, 30 | 20 | 23 |
| 13 | 1000 | 40 | 250 | 80 | 500 | 250 | 23 | 30 | 23 | 27 |
| 14 | 1000 | 40 | 250 | 80 | 500 | 250 | 20 | 27 | 20 | 33 |
| 15 | 1000 | 40 | 250 | 80 | 500 | 250 | 20 | 25 | 20 | 30 |
| 16 | 1000 | 40 | 250 | 80 | 500 | 250 | 20 | 27 | 20 | 25 |
| 17 | 1000 | 40 | 250 | 80 | 500 | 250 | 20 | 25 | 20 | 25 |
| 18 | 1000 | 40 | 250 | 80 | 500 | 250 | 20, 20 | 50, 35 | 20 | 33 |
| 19 | 1000 | 40 | 250 | 80 | 500 | 250 | 20 | 30 | 25, ND, 20 | 60, ND, 33 |
| 20 | 1000 | 40 | 250 | 80 | 500 | 250 | 20 | 25 | 20 | 25 |
| 21 | 1000 | 40 | 250 | 80 | 500 | 250 | 20 | 25 | 20 | 33 |
| 22 | 1000 | 40 | 250 | 80 | 500 | 250 | 20 | 25 | 20 | 25 |
| 23 | 1000 | 40 | 250 | 80 | 500 | 250 | 20 | 27 | 20 | 30 |
| 24 | 1000 | 40 | 250 | 80 | 500 | 250 | 20 | 23 | 20 | 23 |

ND: No detection

TABLE 3

Real-time PCR amplification Ct values are shown for both 500 μl and 700 μl lysate inputs. Five μl of the eluted DNA used in the PCR reaction. ND denotes no Ct value obtained.

| Urine Sample # | Sample (μl) | Assay control (μl) | Lysis buffer (μl) | 1M NaOH (μl) | Column input (μl) | Column Output (μl) | 500 μl lysate load in to the column Ct Value | 700 μl lysate load in to the column Ct Value |
|---|---|---|---|---|---|---|---|---|
| 1 | 1000 | 40 | 250 | 80 | 500 | 250 | 44 | 39 |
| 2 | 1000 | 40 | 250 | 80 | 500 | 250 | 35 | 32 |
| 3 | 1000 | 40 | 250 | 80 | 500 | 250 | ND | ND |
| 4 | 1000 | 40 | 250 | 80 | 500 | 250 | 39 | 36 |
| 5 | 1000 | 40 | 250 | 80 | 500 | 250 | 41 | 37 |

TABLE 3-continued

Real-time PCR amplification Ct values are shown for both 500 μl and 700 μl lysate inputs. Five μl of the eluted DNA used in the PCR reaction. ND denotes no Ct value obtained.

| Urine Sample # | Sample (μl) | Assay control (μl) | Lysis buffer (μl) | 1M NaOH (μl) | Column input (μl) | Column Output (μl) | 500 μl lysate load in to the column Ct Value | 700 μl lysate load in to the column Ct Value |
|---|---|---|---|---|---|---|---|---|
| 6 | 1000 | 40 | 250 | 80 | 500 | 250 | 47 | ND |
| 7 | 1000 | 40 | 250 | 80 | 500 | 250 | 50 | 39 |
| 8 | 1000 | 40 | 250 | 80 | 500 | 250 | 40 | 41 |
| 9 | 1000 | 40 | 250 | 80 | 500 | 250 | 34 | 31 |
| 10 | 1000 | 40 | 250 | 80 | 500 | 250 | 48 | 38 |
| 11 | 1000 | 40 | 250 | 80 | 500 | 250 | 38 | 33 |
| 12 | 1000 | 40 | 250 | 80 | 500 | 250 | ND | 41 |
| 13 | 1000 | 40 | 250 | 80 | 500 | 250 | 43 | 42 |
| 14 | 1000 | 40 | 250 | 80 | 500 | 250 | 42 | 34 |
| 15 | 1000 | 40 | 250 | 80 | 500 | 250 | 43 | 35 |
| 16 | 1000 | 40 | 250 | 80 | 500 | 250 | 44 | 36 |
| 17 | 1000 | 40 | 250 | 80 | 500 | 250 | 40 | 34 |
| 18 | 1000 | 40 | 250 | 80 | 500 | 250 | 35 | 33 |
| 19 | 1000 | 40 | 250 | 80 | 500 | 250 | 40 | 36 |
| 20 | 1000 | 40 | 250 | 80 | 500 | 250 | 39 | 32 |
| 21 | 1000 | 40 | 250 | 80 | 500 | 250 | 44 | 29 |
| 22 | 1000 | 40 | 250 | 80 | 500 | 250 | 34 | 37 |
| 23 | 1000 | 40 | 250 | 80 | 500 | 250 | 34 | 30 |
| 24 | 1000 | 40 | 250 | 80 | 500 | 250 | 43 | 35 |

ND: No Ct value obtained

Example 13

Sample Elution Using Vacuumed Container Instead of Gravity Combined with Detection by LAMP Use of vacuum can be achieved by using a prepackaged container with a closure that maintains a vacuum. A BD Vacutainer was used to demonstrate the application. The SEC media utilized was Sephacryl S-300 in 1×RB. The container used was a 10 ml syringe with a luer lock fitting and a 26 gauge needle and filters to keep the media in the container. The container was filled with 1.1 ml of SEC media.

The application experiment was done using contrived clinical specimens at low concentrations. The clinical matrix was urine and the target was *Chlamydia* cells. Assay Control was added to the specimens, followed by the lysis buffer. Once mixed, 500 ul of lysed specimen was added to the media and drained by gravity. Once sample flow had stopped the target nucleic acid was collected by puncturing a Vacutainer. The Vacutainer pulled the interstitial fluid from the exterior of the media and left the internal fluid in the Sephacryl bead. This material was then tested using illumigene CT devices demonstrating successful amplification. See results in Table 1.

TABLE 1

Results of Application Experiment

| Contrived Specimen | illumigene Test Result (n = 5) | illumigene Control Result (n = 5) |
|---|---|---|
| CT (3 IFU) | 5 Positive (3@22, 2@24) | 5 Positive (4@22, 1@24) |
| CT (1 IFU) | 5 Positive (4@20, 1@24) | 5 Positive (2@22, 3@24) |

What is claimed is:

1. A method of detecting a nucleic acid present in a biological sample, comprising the steps of:
   a) combining the biological sample with a lysis buffer to form a lysis mixture comprising nucleic acid released from cells in said biological sample;
   b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than 10 minutes to produce an eluted solution comprising isolated nucleic acid, wherein the lysis mixture is directly applied to the column without an intervening treatment step between lysis and column application, and wherein the chromatography column has been equilibrated with a reaction buffer used for a subsequent amplification method or any other enzyme-catalyzed reaction;
   c) combining the eluted solution with nucleic acid amplification reagents comprising DNA polymerase, oligonucleotides and nucleoside triphosphates for nucleic acid amplification;
   d) amplifying the nucleic acid in the eluted solution; and
   e) detecting products of nucleic acid amplification.

2. The method of claim 1, wherein the reaction buffer comprises 1-10 mM $Mg^{2+}$ or a non-ionic detergent, or a combination thereof.

3. The method of claim 1, wherein said lysis buffer comprises alkali hydroxide at pH>11.

4. The method of claim 1, wherein said lysis buffer comprises urea or chaotropic salt.

5. The method of claim 1, wherein said lysis buffer separates double stranded nucleic acid into single stranded nucleic acid and inhibits nucleic acid interactions with protein.

6. The method of claim 1, wherein said size-exclusion medium comprises polyacrylamide, polybisacrylamide or polymethacrylamide.

7. The method of claim 1, wherein said nucleic acid is DNA, RNA, or a mixture thereof.

8. The method of claim 1, wherein said amplifying step is selected from the group consisting of RT-PCR, qPCR, digital PCR, LAMP, sequencing, and an enzyme-catalyzed reaction.

9. The method of claim 1, wherein said biological sample is blood, saliva, stool, urine, respiratory sample, or enriched culture broth.

10. The method of claim 1, wherein said size-exclusion medium has a molecular size exclusion limit of about 10kDa or more.

11. The method of claim 1, wherein flow rate of separation is gravity-based.

12. A method of purifying a nucleic acid from a biological sample, comprising the steps of:
   a) combining the biological sample with a lysis buffer to form a lysis mixture comprising nucleic acid released from cells in said biological sample; and
   b) subjecting a volume of the lysis mixture to size-exclusion chromatography in a column comprising a volume of size-exclusion medium, wherein said volume of lysis mixture is 0.01 to 0.6 of the volume of the size-exclusion medium, and having a flow rate of separation of less than 10 minutes to produce an eluted solution comprising isolated nucleic acid, wherein the lysis mixture is directly applied to the column without an intervening treatment step between lysis and column application, and wherein the chromatography column has been equilibrated with a reaction buffer used for a subsequent amplification method or any other enzyme-catalyzed reaction.

13. The method of claim 12, wherein flow rate of separation is gravity-based.

14. The method of claim 12, wherein said nucleic acid is DNA, RNA, or a mixture thereof.

15. The method of claim 12, further comprising equilibrating said chromatography column with an equilibrating buffer comprising 1-10 mM $Mg^{2+}$ or a non-ionic detergent, or a combination, prior to the subjecting of step b).

16. The method of claim 12, wherein said lysis buffer comprises alkali hydroxide at pH >11.

17. The method of claim 12, wherein said lysis buffer comprises urea or chaotropic salt.

18. The method of claim 12, wherein said lysis buffer separates double stranded nucleic acid into single stranded nucleic acid and inhibits nucleic acid interactions with protein.

19. The method of claim 12, wherein said size-exclusion medium comprises polyacrylamide, polybisacrylamide or polymethacrylamide.

20. The method of claim 12, wherein said nucleic acid is DNA, RNA, or a mixture thereof.

21. The method of claim 12, further comprising the later step of analyzing said isolated nucleic acid using an enzyme-catalyzed reaction.

22. A method of purifying nucleic acids, comprising the steps of:
   a) combining the biological sample with a lysis buffer to form a lysis mixture comprising nucleic acid released from cells in said biological sample;
   b) applying a volume of the sample containing nucleic acids to size-exclusion chromatography medium in a column comprising a loading end, an eluting end, and a volume of size-exclusion medium, and allowing sample to enter the size-exclusion chromatography medium, wherein the lysis mixture is directly applied to the column without an intervening treatment step between lysis and column application, and wherein the chromatography column has been equilibrated with a reaction buffer used for a subsequent amplification method or any other enzyme-catalyzed reaction; and
   c) providing a negative pressure differential or vacuum to the eluting end of the column and collecting drained fluid containing nucleic acid for further amplification or analysis.

23. The method of claim 22 wherein the sample containing nucleic acids comprises a lysis mixture obtained from a biological sample.

24. The method of claim 22, wherein the sample enters the SEC medium by gravity flow.

25. The method of claim 22, wherein said nucleic acid is DNA, RNA, or a mixture thereof.

26. The method of claim 22, wherein the reaction buffer comprises 1-10 mM $Mg^{2+}$ or a non-ionic detergent, or a combination thereof.

27. The method of claim 23, wherein said lysis buffer comprises alkali hydroxide at pH>11.

28. The method of claim 23, wherein said lysis buffer comprises urea or chaotropic salt.

29. The method of claim 23, wherein said lysis buffer separates double stranded nucleic acid into single stranded nucleic acid and inhibits nucleic acid interactions with protein.

30. The method of claim 22, wherein said size-exclusion medium comprises polyacrylamide, polybisacrylamide or polymethacrylamide.

31. The method of claim 22, wherein said nucleic acid is DNA, RNA, or a mixture thereof.

32. The method of claim 22, further comprising the later step of analyzing said isolated nucleic acid using an enzyme-catalyzed reaction.

33. A method of purifying a nucleic acid from a biological sample, comprising the steps of:
   a) combining the biological sample with a denaturing solution that separates strands of double-stranded DNA;
   b) subjecting a volume of the biological sample mixture to size-exclusion chromatography in a column comprising a volume of size-exclusion medium, wherein said volume of lysis mixture is 0.01 to 0.6 of the volume of the size-exclusion medium, and having a gravity-based flow rate of separation of less than 10 minutes to produce an eluted solution comprising isolated nucleic acid, wherein the biological sample denatured by the denaturing solution is directly applied to the column without an intervening treatment step between denaturing and column application, and wherein the chromatography column has been equilibrated with a reaction buffer used for a subsequent amplification method or any other enzyme-catalyzed reaction; and
   c) collecting the eluted solution for further amplification or analysis.

* * * * *